US00PP35826P2

(12) United States Plant Patent
Radler

(10) Patent No.: US PP35,826 P2
(45) Date of Patent: May 28, 2024

(54) SHRUB ROSE PLANT NAMED 'RADSLAM'

(50) Latin Name: *Rosa hybrida*
Varietal Denomination: Radslam

(71) Applicant: The Conard Pyle Company, West Grove, PA (US)

(72) Inventor: William Radler, Greenfield, WI (US)

(73) Assignee: THE CONARD PYLE COMPANY, West Grove, PA (US)

( * ) Notice: Subject to any disclaimer, the term of this patent is extended or adjusted under 35 U.S.C. 154(b) by 71 days.

(21) Appl. No.: 18/091,515

(22) Filed: Dec. 30, 2022

(51) Int. Cl.
*A01H 5/02* (2018.01)
*A01H 6/74* (2018.01)

(52) U.S. Cl.
USPC ..... Plt./105

(58) Field of Classification Search
USPC ..... Plt./101, 102, 105
See application file for complete search history.

(56) References Cited

U.S. PATENT DOCUMENTS

PP18,473 P2 2/2008 Carruth
PP30,509 P2 5/2019 Kordes

*Primary Examiner* — Karen M Redden
(74) *Attorney, Agent, or Firm* — Panitch Schwarze Belisario & Nadel LLP; Stephany G. Small; Travis W. Bliss

(57) ABSTRACT

A new and distinct variety of shrub rose plant, referred to by its cultivar name, 'Radslam', is disclosed. The new variety forms attractive, double orange-colored flowers. Attractive semi-glossy foliage is formed, which contrasts beautifully with the blossoms. A very bushy and upright growth habit is displayed. The new variety is well suited for providing attractive ornamentation in the landscape.

1 Drawing Sheet

Latin name of genus and species of plant claimed: *Rosa hybrida.*

Variety denomination: 'Radslam'.

BACKGROUND OF THE INVENTION

The new variety of rose plant of the present invention was created by controlled breeding in June 2015 at Milwaukee, Wisconsin by artificial pollination wherein two parents were crossed which previously had been studied in the hope that they would contribute the desired characteristics. The female parent (i.e., the seed parent) of the new variety was the 'Radhope' variety (not patented). The male parent (i.e., the pollen parent) of the new variety was the 'WEKvossutono' variety (U.S. Plant Pat. No. 18,473).

The parentage of the new variety can be summarized as follows:

'Radhope' x 'WEKvossutono'

The seeds resulting from the above pollination were sown and small plants were obtained which were physically and biologically different from each other. Selective study resulted in the identification of a single plant of the new variety.

The new variety has been found to undergo asexual propagation in Wasco, California and Cochranville, Pennsylvania by vegetative cuttings. Asexual propagation by vegetative cuttings in Wasco, California and Cochranville, Pennsylvania has shown that the characteristics of the new variety are stable and are strictly transmissible by asexual propagation from one generation to another. Accordingly, the new variety undergoes asexual propagation in a true-to-type manner.

SUMMARY OF THE INVENTION

It was found that the new variety of rose plant of the present invention possesses the following combination of characteristics:

(a) forms attractive, orange-colored blossoms,
(b) exhibits a very bushy and upright growth habit, and
(c) displays attractive ornamental semi-glossy foliage.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'Radhope' variety (i.e., seed parent) displays a less compact growth habit compared to the new variety. In addition, the 'WEKvossutono' variety (i.e., pollen parent) exhibits a less upright growth habit compared to the new variety and produces butter gold colored flowers, whereas the new variety produces orange-colored flowers. Moreover, the new variety can be readily distinguished from other similar non-parental varieties. For example, the 'KORcracfir' variety (U.S. Plant Pat. No. 30,509) produces darker colored foliage and exhibits flowers with less petals compared to the new variety.

The new variety has been named 'Radslam'.

BRIEF DESCRIPTION OF THE PHOTOGRAPH

The accompanying photograph of the drawing shows as nearly true as it is reasonably possible to make the same, in a color illustration of this character, a typical specimen of the plant parts of the new variety. The rose plant of the new variety was approximately three years of age and was observed during June 2021 while budded on its own roots and growing outdoors in a field at Cochranville, Pennsylvania, U.S.A.

The drawing sheet illustrates a specimen of the plant displaying flowers at varying points of opening.

DETAILED BOTANICAL DESCRIPTION

The chart used in the identification of the colors is that of The Royal Horticultural Society (The R.H.S. Colour Chart, 2015 edition), London, England. The terminology which precedes reference to the chart has been added to indicate the corresponding color in more common terms. The description is based on the observation of two-years-old specimens of the new variety during January while growing on their own roots in a greenhouse in a three-gallon container at Cochranville, Pennsylvania.

Botanical classification: *Rosa hybrida* cultivar Radslam.

Commercial classification: Shrub Rose Plant.

Plant:

*Habit*.—Very bushy and upright.

*Height*.—Approximately 52.0 cm on average from the top of the soil plane.

*Width*.—Approximately 48.0 cm on average.

Branches:

*Color*.—Young stems: commonly near Green Group 143A. — old wood: commonly near Green Group 138A.

*Length*.—Main stems: approximately 23.0 cm on average. — secondary stems: approximately 15.0 cm on average.

*Diameter*.—Main stems: approximately 7.0 mm on average. — secondary stems: approximately 3.0 mm on average.

*Thorns*.—Amount: moderate, 3 to 4 per internode. — young thorns — color commonly near Yellow-Green Group 151A. — young thorns — size: length is approximately 6.0 mm on average and width is approximately 3.0 mm on average at point of attachment. — old thorns — color commonly near Greyed-Orange Group 177A. — old thorns — size: length is approximately 6.0 mm on average and width is approximately 3.0 mm on average at point of attachment.

Foliage:

*General appearance*.—Vigorous, very dense, with a semi-glossy aspect.

*Number of leaflets*.—3, 5, and 7.

5 *leaflets leaf*.—Length: approximately 11.0 cm on average. — width: approximately 10.0 cm on average.

*Terminal leaflet*.—Length: approximately 6.3 cm on average. — width: approximately 3.8 cm on average.

*Lower leaflets*.—Length: approximately 4.0 cm on average. — width: approximately 2.5 cm on average.

*Young foliage*.—Upper surface color: commonly near Green Group 139A with indistinguishable venation. — under surface color: commonly near Green Group 137B with indistinguishable venation.

*Old foliage*.—Upper surface color: commonly near Green Group 137A with indistinguishable venation. — under surface color: commonly near Yellow-Green Group 147B with venation of near Greyed-Orange Group 172A.

Leaflets:

*Shape*.—Ovate. — apex: acute to acuminate. — base: cuneate.

*Texture*.—Upper and under surfaces are smooth.

*Margin*.—Serrate.

*Undulation on the margin*.—Moderate.

*Petiole rachis*.—Color of upper surface: commonly near Green Group 137A. — color of under surface: commonly near Yellow-Green Group 144A. — length: approximately 8.0 cm on average. — diameter: approximately 1.0 mm on average

*Petioles*.—Texture: upper and under surfaces are smooth. — color of upper surface: commonly near Green Group 137A. — color of under surface: commonly near Yellow-Green Group 144A. — length: approximately 3.0 cm on average. — diameter approximately 1.0 mm on average.

*Stipules*.—Length: approximately 1.5 cm on average. — width: approximately 5.0 mm on average. — margin: entire to erose. — color of upper surface: commonly near Green Group 143B. — color of lower surface: commonly near Green Group 143C.

Inflorescence:

*Number of flowers per plant*.—Approximately 28 blooms on average on a plant at once.

*Number of flowers per stem*.—Typically, between two to four blooms per stem on average.

*Bud*.—Shape: ovoid. — length: approximately 1.5 cm on average. — width: approximately 1.3 cm on average. — color (when opening): commonly near Orange-Red Group 31A.

*Sepals*.—Number: commonly 5. — length: approximately 1.5 cm on average. — width: approximately 9.0 mm on average. — shape: apex: acute to aristate. base: truncate as it joins the receptacle. — margin: entire with extension on two or three sepals measuring 5.0 mm in length and 1.0 mm in width. — upper surface: texture: covered in short pubescence. color commonly near Green Group 143A. — under surface: texture: puberulent. color: commonly near Yellow-Green Group 148C.

*Receptacle*.—Color: commonly near Green Group 143A. — diameter: approximately 8.0 mm on average. — depth: approximately 6.0 mm on average. — surface texture: smooth. — shape: urn shaped.

*Peduncle*.—Length: approximately 4.0 cm on average. — width: approximately 3.0 mm on average. — surface texture: smooth with a few small prickles. — color: commonly near Green Group 143A.

*Flower*.—Form: double, cuplike. — profile: flat to slightly concave as it opens. — diameter: approximately 6.5 cm on average. — height: approximately 2.7 cm on average. — number of petals under normal conditions: 42 on average. — petals: shape: overall shape is broadly obovate; apex shape is rounded to slightly cuspidate; and base shape is cuneate. length: approximately 3.0 cm on average. width: approximately 3.4 cm on average. — petal margin: entire with moderate undulation. — petal drop: good. — flower duration: on the plant approximately 10 to 12 days. — fragrance: slight sweet scent. color when first and fully opened: — upper surface of petal: commonly near Red Group 39B with a medium sized basal spot near Yellow Group 6A. under surface of petal: commonly near Orange Group 29C with a medium sized basal spot near Yellow Group 6C. — color at the end of blooming: upper surface of petal: commonly near Red Group 55B with a medium sized basal spot near Yellow Group 2D. under surface of petal: commonly largely near Red Group 49D transitioning to near Red Group 56A towards petal margin with no distinct basal spot. — petaloids: color is commonly mostly near Red Group 39A transitioning to Yellow Group 6A towards the point of attachment; number is 5; length is approximately 1.5 cm on average; and width is approximately 5.0 mm on average. — anthers: number is 120 on average, length is approximately 3.0 mm on average, coloration is commonly near Yellow-Orange Group 20A, and shape is oval. — filaments: length is approximately 2.0 mm on average and coloration is commonly near Yellow Group 12A. — pistils: arrangement is separate and free and number is approximately 96 on average. — styles: length is approximately 4.0 mm on average, coloration is commonly near Yellow Group 9C. — stigmas: diameter is approximately 1.0 mm on average and shape is fan shaped. — pollen: color is commonly near Yellow-Orange Group 20A and amount is sparse. — hips: not available at this stage.

Development:

*Vegetation*.—Vigorous and strong.

*Blooming*.—Abundant and substantially continuous from spring through frost; typically in bloom outdoors from May to November in Southeastern Pennsylvania.

*USDA hardiness zone*.—Hardy to at least USDA Zone 5.

*Resistance to disease*.—Excellent for black spot (*Diplocarpon rosae*), powdery mildew (*Sphaerotheca pannosa*), and rust (*Phragmidium* sp).

The new 'Radslam' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of shrub rose plant named 'Radslam' characterized by the following combination of characteristics:

(a) forms attractive, orange-colored blossoms, (b) exhibits a very bushy and upright growth habit, and (c) displays attractive ornamental semi-glossy foliage;

substantially as herein shown and described.

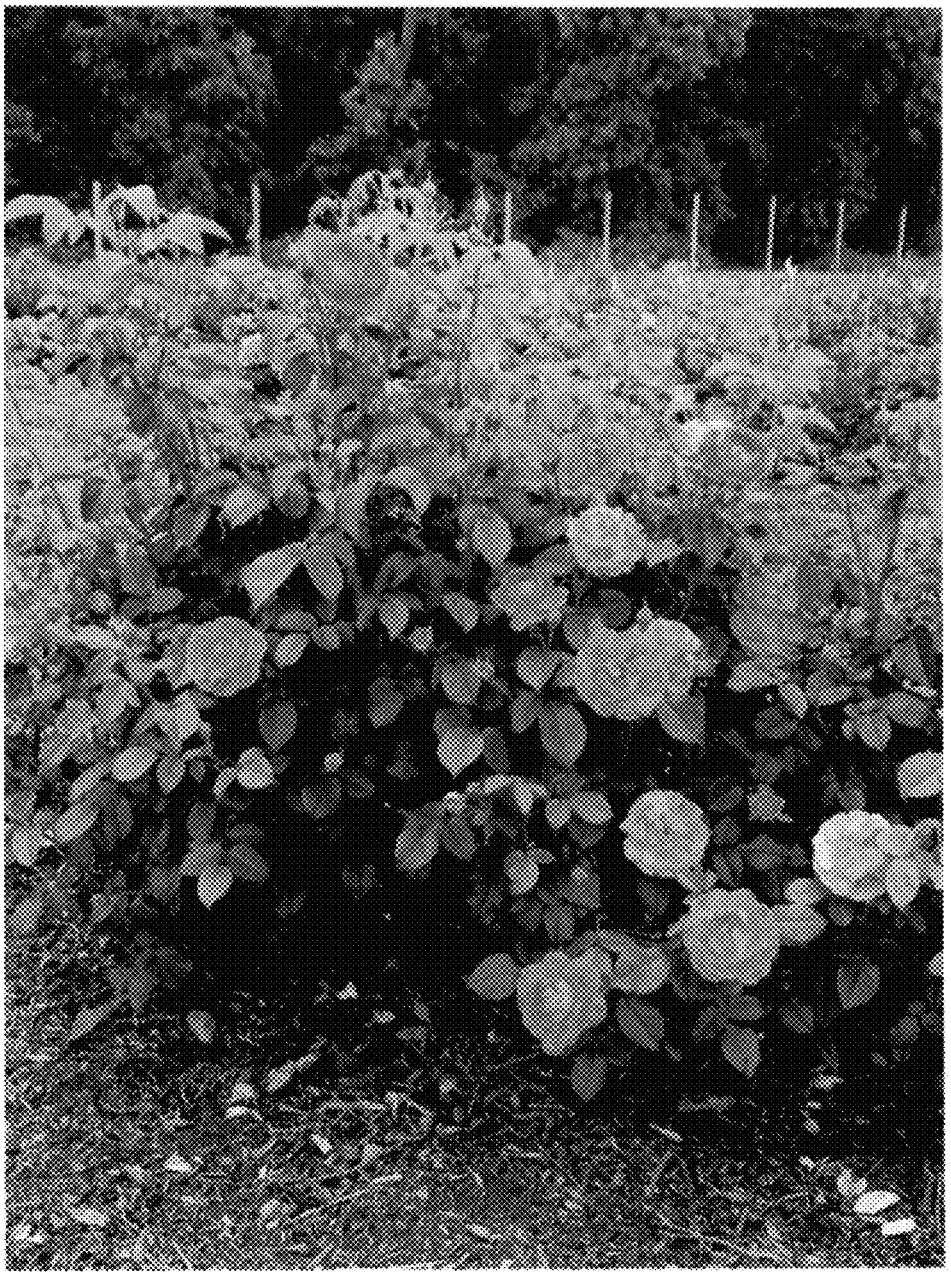

* * * * *